United States Patent
Xu

(10) Patent No.: US 7,595,275 B2
(45) Date of Patent: Sep. 29, 2009

(54) CATALYST COMPOSITIONS AND THEIR SYNTHESIS

(75) Inventor: Teng Xu, Houston, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 325 days.

(21) Appl. No.: 11/504,196

(22) Filed: Aug. 15, 2006

(65) Prior Publication Data
US 2008/0045402 A1 Feb. 21, 2008

(51) Int. Cl.
*B01J 29/06* (2006.01)
(52) U.S. Cl. .............................. 502/60; 502/73; 502/74; 502/75; 502/214
(58) Field of Classification Search .................. 502/73, 502/74, 75, 214
See application file for complete search history.

(56) References Cited

U.S. PATENT DOCUMENTS

| | | | |
|---|---|---|---|
| 4,302,622 A | 11/1981 | Chu | |
| 4,399,059 A | 8/1983 | Chu | |
| 4,440,871 A | 4/1984 | Lok et al. | |
| 4,465,889 A | 8/1984 | Anthony et al. | |
| 4,499,327 A | 2/1985 | Kaiser | |
| 4,590,323 A | 5/1986 | Chu | |
| 4,677,242 A | 6/1987 | Kaiser | |
| 4,677,243 A | 6/1987 | Kaiser | |
| 4,873,390 A | 10/1989 | Lewis et al. | |
| 4,929,763 A | 5/1990 | Luetkens, Jr. et al. | |
| 5,043,308 A | 8/1991 | Luetkens, Jr. et al. | |
| 5,095,163 A | 3/1992 | Barger | |
| 5,130,114 A | 7/1992 | Igarashi | |
| 5,189,198 A | 2/1993 | Kumazawa et al. | |
| 5,714,662 A | 2/1998 | Vora et al. | |
| 6,007,407 A | 12/1999 | Rutherford et al. | |
| 6,017,442 A | 1/2000 | Wu et al. | |
| 6,166,282 A | 12/2000 | Miller | |
| 6,175,048 B1 | 1/2001 | Wu et al. | |
| 6,180,828 B1 | 1/2001 | Hidaka et al. | |
| 6,287,527 B1 | 9/2001 | Kawanami et al. | |
| 6,600,056 B1 | 7/2003 | Mikawa et al. | |
| 6,844,291 B2 | 1/2005 | Levin et al. | |
| 6,906,232 B2 | 6/2005 | Levin et al. | |
| 6,951,830 B2 | 10/2005 | Janssen | |
| 2003/0171633 A1 | 9/2003 | Xu et al. | |
| 2003/0181325 A1 | 9/2003 | Ou et al. | |
| 2005/0020435 A1 | 1/2005 | Beck et al. | |
| 2005/0054517 A1 | 3/2005 | Xu et al. | |
| 2005/0096214 A1 | 5/2005 | Janssen et al. | |
| 2005/0101818 A1 | 5/2005 | Levin et al. | |
| 2006/0004240 A1 | 1/2006 | Xu et al. | |
| 2006/0084568 A1 * | 4/2006 | Filimonov et al. | ............ 502/65 |

FOREIGN PATENT DOCUMENTS

EP 1478464 9/2003

* cited by examiner

*Primary Examiner*—Elizabeth D Wood
(74) *Attorney, Agent, or Firm*—Kevin M. Faulkner; David M. Weisberg

(57) ABSTRACT

The present invention relates to molecular sieve compositions and a process to synthesize such compositions. More particularly, this invention relates to a catalyst composition with metal oxide deposited on the exterior surface of the molecular sieve particles. The metal oxide can be deposited by contacting the molecular sieve particles with a solution of a metal-containing salt and a solvent, the metal-containing salt solution having an anion size larger than the pore size of the molecular sieve particles. The molecular sieve particles can then be dried and then treated under conditions sufficient to form a metal oxide, whereby at least a portion of the metal-containing salt can be converted to metal oxide.

54 Claims, No Drawings ized pores
CATALYST COMPOSITIONS AND THEIR SYNTHESIS

FIELD OF THE INVENTION

The present invention relates to molecular sieve catalyst compositions and a process to synthesize such compositions.

BACKGROUND OF THE INVENTION

There are wide varieties of molecular sieves for use in commercial petroleum and petrochemical industry processes. Molecular sieves are porous solids having pores of varying sizes. The most commercially useful molecular sieves are known as zeolites. Zeolites in general have a three-dimensional crystalline pore structure having uniformly sized pores of molecular dimensions that selectively adsorb molecules that can enter the pores, and exclude those molecules that are too large.

Examples of zeolite molecular sieves are aluminosilicates and metalloaluminophosphates, such as silicoaluminophosphates (SAPOs). SAPO molecular sieves contain a three-dimensional microporous crystalline framework structure of $[SiO_4]$, $[AlO_4]$ and $[PO_4]$ corner-sharing tetrahedral units. SAPO synthesis is described in U.S. Pat. No. 4,440,871, which is herein fully incorporated by reference. SAPO molecular sieves are generally synthesized by the hydrothermal crystallization of a reaction mixture of silicon-, aluminum- and phosphorus-sources and at least one templating agent. Synthesis of a SAPO molecular sieve, its formation into a catalyst, and its use in a process for converting feedstock into olefin(s), particularly where the feedstock is methanol, are disclosed in a large number of granted patents and pending patent applications, including for example, U.S. Pat. Nos. 4,499,327; 4,677,242; 4,677,243; 4,873,390; 5,095,163; 5,714,662 and 6,166,282 and U.S. Patent Application Publication Nos. 2005/0096214 and 2005/0101818 (all incorporated herein by reference).

Typically, molecular sieves are formed into molecular sieve catalyst compositions to improve their durability in commercial processes. These molecular sieve catalyst compositions are formed by combining the molecular sieve and a matrix material usually in the presence of a binder. The purpose of the binder is to hold the matrix material, often clay, to the molecular sieve. Binders and matrix materials typically only serve to provide desired physical characteristics to the catalyst composition, and have little to no effect on conversion and selectivity of the molecular sieve.

A number of metal oxides or mixed metal oxides have been shown to be active for reducing coke selectivity of molecular sieve catalysts (by increasing catalyst lifetime). Some previous work involved 1) the preparation of metal oxides or mixed metal oxides and 2) physically mixing thus-prepared oxides with a catalyst such as SAPO-34. This method of preparation of the catalyst composition is not the most economical, and sometimes presents significant challenges to catalyst formulation, such as uniformity, performance and efficiency.

U.S. Pat. No. 6,180,828 discusses the use of a modified molecular sieve to produce methylamines from methanol and ammonia where, for example, a silicoaluminophosphate molecular sieve is combined with one or more modifiers, such as zirconium oxide, a titanium oxide, yttrium oxide, montmorillonite or kaolinite.

U.S. Pat. No. 4,465,889 describes a catalyst composition comprising a silicate molecular sieve impregnated with thorium, zirconium, or titanium metal oxide for use in converting methanol, dimethyl ether, or a mixture thereof into a hydrocarbon product rich in iso-$C_4$ compounds.

U.S. Pat. No. 6,906,232 relates to a conversion process of a feedstock, preferably an oxygenated feedstock, into one or more olefin(s), preferably ethylene and/or propylene, in the presence of a molecular sieve catalyst composition that includes a molecular sieve and a Group 3 metal oxide and/or an oxide of a Lanthanide or Actinide series element. The invention is also directed to methods of making and formulating the molecular sieve catalyst composition useful in a conversion process of a feedstock into one or more olefin(s).

Other patents and publications of relevance to this invention include: U.S. Pat. Nos. 6,906,232; 6,844,291; 6,951,830; 4,302,622; 4,590,323; 4,929,763; 5,043,308; 5,130,114; 5,189,198; 6,017,442; 6,287,527; and 6,600,056, European Patent No. 1478464, U.S. Patent Publication Nos. 2003/0171633; 2003/0181325; 2005/0054517 and 2005/0020435.

Molecular sieve catalysts, including SAPO molecular sieve catalysts, require frequent regeneration due to coking and therefore have limited lifetimes. Coking occurs when coke deposits either directly (site coverage) and/or indirectly (pore blockage) decrease the number of active sites available for the conversion reaction in the reactor. Although some level of coke has been found to be beneficial, coking typically decreases catalyst lifetime and is a common cause of catalyst deactivation.

Regeneration is the process whereby at least a portion of the molecular sieve's initial activity is recovered by combusting and removing at least a portion of the coke deposits on the catalyst with agents such as air, hydrogen, steam, or carbon monoxide, alone or in combination. This process is very expensive, time consuming and adds extra steps to the processing of the feedstock. It would be beneficial to reduce the coking on the catalyst, thereby increasing catalyst lifetime and reducing the need for regeneration, which would decrease the cost of the entire conversion process. Therefore, any means for reducing coke selectivity or increasing catalyst lifetime would result in significant investment savings.

It would also be desirable to have an improved molecular sieve catalyst composition having a better conversion rate, improved olefin selectivity and a longer lifetime.

The present invention satisfies these needs by providing a molecular sieve catalyst composition and a method for preparing the molecular sieve catalyst composition in which a solution of metal-containing salt is mixed with the molecular sieve followed by drying and calcination of the mixture. The metal-containing salt solution comprises an anion larger than the pore diameter of the molecular sieve. Accordingly, the metal-containing salt is deposited substantially only on the exterior surface of the molecular sieve particles. This process results in equal or longer catalyst lifetime when compared with molecular sieve catalyst compositions currently in use.

SUMMARY OF THE INVENTION

This invention relates to a catalyst composition comprising: a first quantity of molecular sieve particles, each of the molecular sieve particles having an exterior surface, at least an 8-ring or larger structure, and a plurality of pores having a pore size in the range of from about 3 angstroms to about 15 angstroms; and a second quantity of a metal oxide deposited substantially on the exterior surface of the molecular sieve particles, the metal oxide having been deposited by contacting the molecular sieve particles with a solution of a metal-containing salt and a solvent, the metal-containing salt comprising a salt soluble in water or common organic solvents and a metal selected from the group consisting of Groups 1-12 and the Lanthanides of the periodic table and combinations thereof, the metal-containing salt solution having an anion size larger than the pore size of the molecular sieve particles; drying the molecular sieve particles to remove substantially all of the solvent, thereby depositing the metal-containing salt substantially on the exterior surface of the molecular sieve particles; and treating the molecular sieve particles under conditions sufficient to form a metal oxide, whereby at least a portion of the metal-containing salt is converted to metal oxide.

This invention also relates to a process for preparing a molecular sieve catalyst composition comprising: obtaining a first quantity of molecular sieve particles, each of the molecular sieve particles having an exterior surface, an 8-ring or larger structure, and a plurality of pores having a pore size in the range of from about 3 angstroms to about 15 angstroms; preparing a second quantity of a solution comprising a metal-containing salt and a solvent, the metal-containing salt comprising a salt soluble in water or common organic solvents and a metal selected from the group consisting of Groups 1-12 and the Lanthanides of the periodic table and combinations thereof, the metal-containing salt solution having an anion size larger than the pore size of the molecular sieve particles; mixing the first quantity of molecular sieve particles with the second quantity of the solution; drying the molecular sieve particles to remove the solvent, thereby depositing the metal-containing salt substantially on the exterior of the molecular sieve particles; and subsequently calcining the molecular sieve particles at a temperature of at least about 200° C. for at least 1 second, whereby the metal-containing salt is at least partially converted to metal oxide.

This invention further relates to a catalyst composition prepared according to a process comprising the steps of: obtaining a first quantity of molecular sieve particles, each of the molecular sieve particles having an exterior surface, an 8-ring or larger structure, and a plurality of pores having a pore size in the range of from about 3 angstroms to about 15 angstroms; preparing a second quantity of a solution comprising a metal-containing salt and a solvent, the metal-containing salt comprising a salt soluble in water or common organic solvents and a metal selected from the group consisting of Groups 1-12 and the Lanthanides of the periodic table and combinations thereof, the metal-containing salt solution having an anion size larger than the pore size of the molecular sieve particles; mixing the first quantity of molecular sieve particles with the second quantity of solution; drying the molecular sieve particles to remove the solvent, thereby depositing the metal-containing salt substantially on the exterior of the molecular sieve particles; and subsequently calcining the molecular sieve particles at a temperature of at least about 200° C. for at least 1 second.

DETAILED DESCRIPTION OF THE PREFERRED EMBODIMENTS

As used herein, "molecular sieve particles" are defined to include the molecular sieve particles alone or the molecular sieve particles as combined with other additives such as a matrix material and/or a binder.

As used herein, "calcination" is the heating of a solid to a temperature below its melting point to bring about a state of thermal decomposition or a phase transition other than melting.

In a preferred embodiment, the molecular sieve catalyst composition is prepared by mixing the molecular sieve particles with a solution of a metal-containing salt and a solvent, the metal-containing salt solution having an anion size larger than the pore size of the molecular sieve particles, drying the molecular sieve particles to remove substantially all of the solvent, thereby depositing the metal-containing salt substantially on the exterior of the molecular sieve particles; and then calcining the molecular sieve particles.

Molecular Sieve

Molecular sieves have various chemical, physical, and framework characteristics and have been well classified by the Structure Commission of the International Zeolite Association according to the rules of the IUPAC Commission on Zeolite Nomenclature. A framework-type describes the topology and connectivity of the tetrahedrally coordinated atoms constituting the framework, and makes an abstraction of the specific properties for those materials. Framework-type zeolite and zeolite-type molecular sieves for which a structure has been established, are assigned a three letter code and are described in the *Atlas of Zeolite Framework Types,* 5th edition, Elsevier, London, England (2001), which is herein fully incorporated by reference.

Non-limiting examples of these molecular sieves are the small pore molecular sieves, AEI, AFT, APC, ATN, ATT, ATV, AWW, BIK, CAS, CHA, CHI, DAC, DDR, EDI, ERI, GOO, KFI, LEV, LOV, LTA, MON, PAU, PHI, RHO, ROG, THO, and substituted forms thereof; the medium pore molecular sieves, AFO, AEL, EUO, HEU, FER, MEL, MFI, MTW, MTT, TON, and substituted forms thereof; and the large pore molecular sieves, EMT, FAU, and substituted forms thereof. Other molecular sieves include ANA, BEA, CFI, CLO, DON, GIS, LTL, MER, MOR, MWW and SOD. Non-limiting examples of the preferred molecular sieves, particularly for converting an oxygenate containing feedstock into olefin(s), include AEL, AEI, AFY, BEA, CHA, EDI, FAU, FER, GIS, LTA, LTL, MER, MFI, MOR, MTT, MWW, TAM and TON. In one preferred embodiment, the molecular sieve of the invention has an AEI topology or a CHA topology, or a combination thereof, most preferably a CHA topology.

Crystalline molecular sieve materials all have a three-dimensional, four-connected framework structure of corner-sharing $TO_4$ tetrahedra, where "T" is any tetrahedrally coordinated cation. These molecular sieves are typically described in terms of the size of the ring that defines a pore, where the size is based on the number of T atoms in the ring. Other framework-type characteristics include the arrangement of rings that form a cage, and when present, the dimension of channels, and the spaces between the cages. See van Bekkum, et al., *Introduction to Zeolite Science and Practice, Second Completely Revised and Expanded Edition,* Volume 137, pages 1-67, Elsevier Science, B.V., Amsterdam, Netherlands (2001).

The small, medium and large pore molecular sieves have from a 4-ring to a 12-ring or greater framework-type. In a preferred embodiment of the invention, the molecular sieves have 8-, 10-, or 12-ring structures or larger and a pore size in the range of from about 3 angstroms to about 15 angstroms. The pore sizes of the molecular sieves are generally uniform. Therefore, as referred to herein, when only one number is mentioned as a pore size, minor variations of that pore size are acceptable.

Molecular sieves, for use with the present invention, have a molecular framework of one, preferably two or more corner-sharing $[TO_4]$ tetrahedral units, and more preferably, two or more $[SiO_4]$, $[AlO_4]$ and/or $[PO_4]$ tetrahedral units. These silicon, aluminum, and phosphorous based molecular sieves and metal containing silicon, aluminum and phosphorous based molecular sieves have been described in detail in numerous publications including for example, U.S. Pat. No. 4,567,029 (MeAPO where Me is Mg, Mn, Zn, or Co), U.S. Pat. No. 4,440,871 (SAPO), European Patent Application EP-A-0 159 624 (ELAPSO where El is As, Be, B, Cr, Co, Ga, Ge, Fe, Li, Mg, Mn, Ti or Zn), U.S. Pat. No. 4,554,143 (FeAPO), U.S. Pat. Nos. 4,822,478, 4,683,217, 4,744,885 (FeAPSO), EP-A-0 158 975 and U.S. Pat. No. 4,935,216 (ZnAPSO), EP-A-0 161 489(CoAPSO), EP-A-0 158 976 (ELAPO, where EL is Co, Fe, Mg, Mn, Ti or Zn), U.S. Pat. No. 4,310,440 (AlPO$_4$), EP-A-0 158 350 (SENAPSO), U.S. Pat. No. 4,973,460 (LiAPSO), U.S. Pat. No. 4,789,535 (LiAPO), U.S. Pat. No. 4,992,250 (GeAPSO), U.S. Pat. No. 4,888,167 (GeAPO), U.S. Pat. No. 5,057,295 (BAPSO), U.S. Pat. No. 4,738,837 (CrAPSO), U.S. Pat. Nos. 4,759,919, and 4,851,106 (CrAPO), U.S. Pat. Nos. 4,758,419, 4,882,038, 5,434,326 and 5,478,787 (MgAPSO), U.S. Pat. No. 4,554, 143 (FeAPO), U.S. Pat. No. 4,894,213 (AsAPSO), U.S. Pat. No. 4,913,888 (AsAPO), U.S. Pat. Nos. 4,686,092, 4,846,956 and 4,793,833 (MnAPSO), U.S. Pat. Nos. 5,345,011 and 6,156,931 (MnAPO), U.S. Pat. No. 4,737,353 (BeAPSO), U.S. Pat. No. 4,940,570 (BeAPO), U.S. Pat. Nos. 4,801,309, 4,684,617 and 4,880,520(TiAPSO), U.S. Pat. Nos. 4,500, 651, 4,551,236 and 4,605,492 (TiAPO), U.S. Pat. Nos. 4,824, 554, 4,744,970 (CoAPSO), U.S. Pat. No. 4,735,806 (GaAPSO) EP-A-0 293 937 (QAPSO, where Q is framework oxide unit [QO2]), as well as U.S. Pat. Nos. 4,567,029; 4,686, 093; 4,781,814; 4,793,984; 4,801,364; 4,853,197; 4,917,876; 4,952,384; 4,956,164; 4,956,165; 4,973,785; 5,241,093; 5,493,066 and 5,675,050, all of which are herein fully incorporated by reference.

Other molecular sieves which may be used in connection with this invention include those described in R. Szostak, *Handbook of Molecular Sieves*, Van Nostrand Reinhold, New York, N.Y. (1992), which is herein fully incorporated by reference.

The more preferred silicon, aluminum and/or phosphorous containing molecular sieves, and aluminum, phosphorous, and optionally silicon, containing molecular sieves include aluminophosphate (AlPO) molecular sieves and silicoaluminophosphate (SAPO) molecular sieves and substituted, preferably metal substituted, AlPO and SAPO molecular sieves. The most preferred molecular sieves for use in connection with the present invention are SAPO molecular sieves, and metal substituted SAPO molecular sieves.

Non-limiting examples of SAPO and AlPO molecular sieves useful in connection with the present invention include one or a combination of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44 (U.S. Pat. No. 6,162,415), SAPO-47, SAPO-56, AlPO-5, AlPO-11, AlPO-18, AlPO-31, AlPO-34, AlPO-36, AlPO-37, AlPO-46, and metal containing forms thereof. Preferably, the molecular sieve is selected from the group consisting of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, the metal containing forms thereof, and mixtures thereof. The more preferred zeolite-type molecular sieves include one or a combination of SAPO-18, SAPO-34, SAPO-35, SAPO-44, SAPO-56, AlPO-18 and AlPO-34, and metal containing forms thereof, even more preferably one or a combination of SAPO-18, SAPO-34, AlPO-34 and AlPO-18, and metal containing forms thereof, and most preferably one or a combination of SAPO-34 and AlPO-18, and metal containing forms thereof. Optionally, the molecular sieve is selected from the group consisting of SAPO-34, the metal containing forms thereof, and mixtures thereof. Another important class of SAPO molecular sieves which may be used in connection with the present invention, consists of mixed or intergrown phases of molecular sieves having the CHA and AEI framework types. Examples of such materials are disclosed in WO 98/15496, published 16 Apr. 1998, in WO 02/070407, published Sep. 12, 2002, and U.S. Pat. No. 6,812,372, all herein fully incorporated by reference.

Each of the crystalline molecular sieves may be used alone or in a mixture with other molecular sieves. This may be not only as a simple mixture, but as an intergrowth, for example, of offretite and erionite as in U.S. Pat. No. 4,086,186, namely an intergrowth of two kinds of crystalline molecular sieves having different topologies from each other.

In one embodiment, the molecular sieve, as described in many of the U.S. Patents mentioned above, is represented by the empirical formula, on an anhydrous basis:

$$mR:(M_xAl_yP_z)O_2$$

wherein R represents at least one templating agent, preferably an organic templating agent; m is the number of moles of R per mole of $(M_xAl_yP_z)O_2$ and m has a value from 0 to 1, preferably 0 to 0.5, and most preferably from 0 to 0.3; x, y, and z represent the mole fraction of Al, P and M as tetrahedral oxides, where M is a metal selected from Groups 1-12 and the Lanthanide's of the Periodic Table of Elements, preferably M is selected from the group consisting of Co, Cr, Cu, Fe, Ga, Ge, Mg, Mn, Ni, Sn, Ti, Zn and Zr. In an embodiment, m is greater than or equal to 0.2, and x, y and z are greater than or equal to 0.01. All numbers and references to the Periodic Table of Elements are based on the new notation as set out in *Chemical and Engineering News*, 63(5), 27 (1985).

In another embodiment, m is from about 0.1 to about 1, x is from about 0.01 to about 0.25, y is from about 0.4 to about 0.5, and z is in the range of from about 0.25 to about 0.5, more preferably m is from about 0.15 to about 0.7, x is from about 0.01 to about 0.2, y is from about 0.4 to about 0.5, and z is from about 0.3 to about 0.5.

Templating agents are generally compounds that contain elements of Group 15 of the Periodic Table of Elements, particularly nitrogen, phosphorus, arsenic and antimony, more preferably nitrogen or phosphorous, and most preferably nitrogen. Typical templating agents also contain at least one alkyl or aryl group, preferably an alkyl or aryl group having from 1 to 10 carbon atoms, and more preferably from 1 to 8 carbon atoms. The preferred templating agents are nitrogen-containing compounds such as amines and quaternary ammonium compounds. Non-limiting examples of templating agents can be found in U.S. Pat. No. 6,906,232, column 8, lines 6-43, incorporated herein by reference.

In another embodiment, the molecular sieve is an intergrowth material having two or more distinct phases of crystalline structures within one molecular sieve composition. In particular, intergrowth molecular sieves are described in the U.S. Patent Publication No. 2002/0165089 and PCT WO 98/15496 published Apr. 16, 1998, both of which are herein fully incorporated by reference. For example, SAPO-18, AlPO-18 and RUW-18 have an AEI framework-type, and SAPO-34 has a CHA framework-type. In another embodiment, the molecular sieve comprises at least one intergrown phase of AEI and CHA framework-types, preferably the molecular sieve has a greater amount of CHA framework-type to AEI framework-type, and more preferably the ratio of CHA to AEI is greater than 1:1 as determined by the DIFFaX method disclosed in U.S. Patent Publication No. 2002/0165089.

The molecular sieve, in a preferred embodiment, is combined with one or more matrix material(s). Matrix materials are typically effective in reducing overall catalyst cost, acting as thermal sinks to assist in shielding heat from the catalyst composition for example during regeneration, densifying the catalyst composition, increasing catalyst strength such as crush strength and attrition resistance, and controling the rate of conversion in a particular process.

Non-limiting examples of matrix materials include one or more of: rare earth metals, metal oxides including titania, zirconia, magnesia, thoria, beryllia, quartz, silica or sols, and mixtures thereof, for example silica-magnesia, silica-zirconia, silica-titania, silica-alumina and silica-alumina-thoria. In an embodiment, matrix materials are natural clays such as those from the families of montmorillonite and kaolin. These natural clays include subbentonites and those kaolins known as, for example, Dixie, McNamee, Georgia and Florida clays. Non-limiting examples of other matrix materials include: haloysite, kaolinite, dickite, nacrite, or anauxite. In one embodiment, the matrix material, preferably any of the clays, are subjected to well known modification processes such as calcination and/or acid treatment and/or chemical treatment.

In one preferred embodiment, the matrix material is a clay or a clay-type composition, preferably a clay or clay-type composition having a low iron or titania content, and most preferably the matrix material is kaolin. Kaolin has been found to form a pumpable, high solid content slurry, it has a low fresh surface area, and it packs together easily due to its platelet structure. A preferred average particle size of the matrix material, most preferably kaolin, is from about 0.1 μm to about 0.6 μm with a D90 particle size distribution of less than about 1 μm. As used herein, average particle size is measured by Atomic Force Microscopy (AFM).

In another embodiment, the binders are alumina sols, predominantly comprising aluminum oxide, optionally including some silicon. In yet another embodiment, the binders are peptized alumina made by treating alumina hydrates such as pseudobohemite, with an acid, preferably an acid that does not contain a halogen, to prepare sols or aluminum ion solutions. Non-limiting examples of commercially available colloidal alumina sols include Nalco 8676 available from Nalco Chemical Co., Naperville, Ill., and Nyacol available from The PQ Corporation, Valley Forge, Pa.

In one embodiment, the binder, templating agent and the molecular sieve and the matrix material are combined to form a molecular sieve catalyst composition. In one embodiment, the weight ratio of the binder to the matrix material used in the formation of the molecular sieve catalyst composition is up to 1:15, preferably 1:4 to 1:15, more preferably 1:5 to 1:10, and most preferably 1:5 to 1:6. It has been found that a higher sieve content, lower matrix content, increases the molecular sieve catalyst composition performance, however, lower sieve content, higher matrix material, improves the attrition resistance of the composition.

The molecular sieve and matrix material, and the optional binder, are combined in any order, together, simultaneously, sequentially, or a combination thereof.

In an embodiment, the average particle size of the molecular sieve is preferably less than about 300 microns, more preferably less than about 200 microns and most preferably less than about 100 microns.

In an embodiment, the pore size of the molecular sieve is from about 3 angstroms to about 15 angstroms, more preferably less than about 12 angstroms, more preferably less than about 10 angstroms, more preferably less than about 8 angstroms, more preferably less than about 6 angstroms, more preferably in the range of from about 3 angstroms to about 5 angstroms, more preferably from about 3 angstroms to about 4.5 angstroms, and most preferably from about 3.5 angstroms to about 4.2 angstroms. As used herein, pore size can be measured by any method known to those skilled in the art.

In an embodiment, structure of the molecular sieve is 8-ring or larger. In another embodiment the structure of the molecular sieve is an 8-, 10-, or 12-ring structure. In yet another embodiment the structure of the molecular sieve is an 8-ring structure.

Solution Comprising Metal-Containing Salt and Solvent

The synthesis of the solution comprising metal-containing salt and solvent is straightforward and first involves the dissolution of the metal-containing salt in a solvent.

A metal-containing salt typically comprises a salt anion and a metal cation. Usable salts of this invention are those with an anion size larger than the size of the molecular sieve pores and those that are soluble in water or in common organic solvents such as methanol or acetone. Typical non-limiting examples of inorganic salts for use in this invention include chlorides, nitrates, sulfates, and phosphates, (as long as they are soluble). Preferably, the salt is organic, such as one or more of: acetylacetonate, hexanoate, naphthenate, naphthoate, iso-oxides such as iso-propoxide, oxalate and combinations thereof. More preferably the salt is chosen from one of: tris(butylcyclopentadienyl)yttrium, tri(n-propylcyclopentadienyl)yttrium, tris(2,2,6,6-tetramethyl-3,5-heptanedionato)yttrium, yttrium (III) 2-ethylhexanoate, yttrium (III) i-propoxide, or combinations thereof.

In a preferred embodiment, the metal is a metal chosen from Groups 1-12 and the Lanthanides of the periodic table, more preferably from Groups 2 and 3, more preferably from Group 3, and most preferably the metal is yttrium.

The metal-containing salt can typically be prepared by any conventional method known in the art or purchased commercially. Examples of some commercially available metal-containing salts usable in this invention include: yttrium (III) 2-ethylhexonate, yttrium (III) naphthoate, yttium (III) naphthenate (60% in toluene), yttrium (III) neodecanoate, yttrium (III) oxalate nonahydrate, yttrium (III) i-propoxide, and combinations thereof. Most preferably, the metal-containing salt for use in this invention is yttrium(III) acetylacetonate ($Y(C_5H_7O_2)_3$).

Solvents useful in this invention include any solvent or solvent mixture that can dissolve the salt. For example, typical useable solvents would be ethers, ketones, such as acetone, hydrocarbons, such as benzene and toluene, alcohols, such as ethanol and propanol, and the like, and combinations thereof. Alternately, water may be used to dissolve the salt.

Process

The process of directly loading a catalyst with metal-containing salts, according to the present invention, is as follows below. The process includes contacting the molecular sieve particles and the metal-containing salt solution, drying the molecular sieve particles to remove substantially all of the solvent and calcination of the metal salt loaded catalyst by carefully controlling the calcination temperature.

In a preferred embodiment of this invention, the molecular sieve particles and the metal-containing salt solution are contacted to form a mixture. After contacting the particles and solution, the combination is then subjected to at the very least some minor mixing to ensure that there is sufficient and even contact between all of the molecular sieve particles and the solution. Mixing may occur through any convention method.

After the molecular sieve particles and the metal-containing salt solution are contacted, the mixture is preferably dried to remove substantially all of the solvent. While not wanting to be bound by theory, it is believed that because the salt anion is larger than the molecular sieve pore size, the metal-salt is deposited predominantly on the exterior surface of the molecular sieve particles. In a preferred embodiment, the metal salt is deposited substantially on the exterior surface of the molecular sieve. In another preferred embodiment, the metal salt is substantially not deposited in the interior surface (e.g. in the pores) of the molecular sieve.

As used herein, "substantially" is defined as at least 95%, preferably at least 98%, more preferably at least 99% and most preferably at least 99.9% by weight. As used herein, "substantially not" is defined as less than 5%, preferably less than 2%, more preferably less than 1%, and most preferably less than 0.1% by weight.

For purposes of this invention, "dried" means that the mixture used to form the molecular sieve catalyst has been submitted to heat in a drying or forming unit but has not been calcined. Calcination is essentially a combustion process that takes place at a higher temperature than that of a drying process. Dried also means that at least a portion of the liquid solvent used during the manufacture of the catalyst has been removed. The method of the invention can be used with molecular sieve catalyst compositions from which the liquid used for manufacture has been partially, substantially or totally removed.

The mixture can be dried using any one or more of many conventional drying methods such as: vacuum oven, spray dryer, exposure to dry gas, or a combination thereof. One preferred method of drying is as described below in the examples, 125° C. for 1 hr in a vacuum oven. However, the drying is not critical in terms of obtaining an effective catalyst. For example, one can probably use temperatures from 80° C. to 150° C. In another embodiment, the drying time can vary, depending on factors such as the drying temperature. The overall objective of the drying process is to remove the solvent prior to calcination.

Once the molecular sieve catalyst composition is formed in a substantially dry or dried state, to further harden and/or activate the formed catalyst composition, a heat treatment such as calcination, at an elevated temperature is usually performed. Typical calcination environments include but are not limited to: air (which may include a small amount of water vapor), nitrogen, helium, flue gas (combustion product lean in oxygen), or any combination thereof. A conventional calcination environment to harden the catalyst particles is air that typically includes a small amount of water vapor.

In one embodiment, calcination of the formulated molecular sieve catalyst composition is carried out in any of a number of well known devices including rotary calciners, fluid bed calciners, batch ovens, and the like. Calcination time is typically dependent on the degree of hardening of the molecular sieve catalyst composition and the temperature.

In a preferred embodiment, the catalyst composition is heated in nitrogen at a temperature of about 200° C. to about 800° C., preferably about 300° C. to about 750° C., more preferably about 400° C. to about 700° C., even more preferably about 500° C. to about 675° C., and most preferably at about 650° C. Heating is carried out for a period of time typically from about 1 second to about 15 hours, such as from about 30 seconds to about 10 hours, from about 1 hour to about 5 hours, and particularly from about 2 hours to about 4 hours.

When a templating agent is used in the synthesis of a molecular sieve, it is preferred that the templating agent is substantially, preferably completely, removed and/or decomposed after crystallization by numerous well known techniques, for example, heat treatments such as calcination to either partially or completely decompose and oxidize the templating agent. As used in this paragraph, "substantially removed" means that at least about 95% is removed, preferably at least about 97%, and most preferably at least about 98%.

Additionally or alternately, the invention contains the following embodiments, which are merely indicative and not meant to limit the scope of the invention in any way.

Embodiment 1

A catalyst composition comprising:
a. a first quantity of molecular sieve particles, each of the molecular sieve particles having
  i. an exterior surface;
  ii. at least an 8-ring or larger structure; and
  iii. a plurality of pores having a pore size in the range of from about 3 angstroms to about 15 angstroms; and
b. a second quantity of a metal oxide deposited substantially on the exterior surface of the molecular sieve particles, the metal oxide having been deposited by
  i. contacting the molecular sieve particles with a solution of a metal-containing salt and a solvent, the metal-containing salt comprising a salt soluble in water or common organic solvents and a metal selected from the group consisting of Groups 1-12 and the Lanthanides and combinations thereof, the metal-containing salt solution having an anion size larger than the pore size of the molecular sieve particles;
  ii. drying the molecular sieve particles to remove substantially all of the solvent, thereby depositing the metal-containing salt substantially on the exterior surface of the molecular sieve particles; and
  iii. treating the molecular sieve particles under conditions sufficient to form a metal oxide, whereby at least a portion of the metal-containing salt is converted to metal oxide.

Embodiment 2

A process for preparing a molecular sieve catalyst composition comprising:
a. obtaining a first quantity of molecular sieve particles, the molecular sieve particles having an exterior surface, an 8-ring or larger structure, and a plurality of pores having a pore size in the range of from about 3 angstroms to about 15 angstroms;
b. preparing a second quantity of a solution comprising a metal-containing salt and a solvent, the metal-containing salt comprising a salt soluble in water or common organic solvents and a metal selected from the group consisting of Groups 1-12 and the Lanthanides and combinations thereof, the metal-containing salt solution having an anion size larger than the pore size of the molecular sieve particles;
c. mixing the first quantity of molecular sieve particles with the second quantity of the solution;
d. drying the molecular sieve particles to remove the solvent, thereby depositing the metal-containing salt substantially on the exterior of the molecular sieve particles; and
e. calcining the molecular sieve particles at a temperature of at least about 200° C. for at least 1 second, whereby the metal-containing salt is at least partially converted to metal oxide.

Embodiment 3

The catalyst composition or process of embodiment 1 or embodiment 2, wherein the step of treating the molecular sieve particles comprises calcining the molecular sieve particles at a temperature of at least about 200° C. for at least about 1 second.

Embodiment 4

The catalyst composition or process of any one of embodiments 1 to 3, wherein the second quantity of a metal oxide is substantially not deposited in the pores of the molecular sieve particles.

Embodiment 5

The catalyst composition or process of any one of embodiments 1 to 4, wherein the molecular sieve particles have a pore system defined by an 8-membered ring of tetrahedra [$TO_4$].

Embodiment 6

The catalyst composition or process of any one of embodiments 1 to 5, wherein the step of contacting the molecular sieve particles with a solution of a metal-containing salt and a solvent comprises mixing the molecular sieve particles and the solution.

Embodiment 7

The catalyst composition or process of any one of embodiments 1 to 6, wherein the molecular sieve particles have a pore size of 5 angstroms or less.

Embodiment 8

The catalyst composition or process of any one of embodiments 1 to 4 or 6 to 7, wherein the molecular sieve particles have a pore system defined by a 10-membered ring of tetrahedra [$TO_4$].

Embodiment 9

The catalyst composition or process of any one of embodiments 1 to 8, wherein the molecular sieve particles are silicoaluminophosphate molecular sieve particles and/or aluminosilicate molecular sieve particles, or mixtures thereof.

Embodiment 10

The catalyst composition or process of any one of embodiments 1 to 9, wherein the molecular sieve particles are of the CHA and/or AEI framework types, or mixtures thereof.

Embodiment 11

The catalyst composition or process of any one of embodiments 1 to 10, wherein the molecular sieve particles have an average particle size of less than about 1 mm.

Embodiment 12

The catalyst composition or process of embodiment 11, wherein the molecular sieve particles have an average particle size of less than about 500 microns.

Embodiment 13

The catalyst composition or process of embodiment 12, wherein the molecular sieve particles have an average particle size of less than about 150 microns.

Embodiment 14

The catalyst composition or process of any one of embodiments 1 to 13, wherein the step of treating the molecular sieve particles comprises calcining at a temperature of from about 200° C. to about 800° C. for at least about 1 second.

Embodiment 15

The catalyst composition or process of embodiment 14, wherein the step of treating the molecular sieve particles comprises calcining at a temperature of about 300° C. to about 750° C. for at least about 1 second.

Embodiment 16

The catalyst composition or process of embodiment 15, wherein the step of treating the molecular sieve particles comprises calcining at a temperature of from about 400° C. to about 700° C. for at least about 1 second.

Embodiment 17

The catalyst composition or process of embodiment 16, wherein the step of treating the molecular sieve particles comprises calcining at a temperature of from about 500° C. to about 675° C. for at least about 1 second.

Embodiment 18

The catalyst composition or process of any one of embodiments 1 to 17, wherein the molecular sieve particles are SAPO-34.

Embodiment 19

The catalyst composition or process of any one of embodiments 1 to 18, wherein the molecular sieve particles have a pore size of about 3 to about 10 angstroms.

Embodiment 20

The catalyst composition or process of embodiment 19, wherein the molecular sieve particles have a pore size of about 3 to about 8 angstroms.

Embodiment 21

The catalyst composition or process of embodiment 20, the molecular sieve particles have a pore size of about 3 to about 4.5 angstroms.

Embodiment 22

The catalyst composition or process of embodiment 21, the molecular sieve particles have a pore size of about 3.5 to about 4.2 angstroms.

Embodiment 23

The catalyst composition or process of any one of embodiments 1 to 22, wherein the molecular sieve particles are crystalline silicoaluminophosphate molecular sieve particles substantially of CHA framework type.

Embodiment 24

The catalyst composition or process of any one of embodiments 1 to 22, wherein the molecular sieve particles are SAPO molecular sieve particles which consist of mixed or intergrown phases of molecular sieves having the CHA and/or AEI framework types.

Embodiment 25

The catalyst composition or process of any one of embodiments 1 to 24, wherein the metal-containing salt is Yttrium (III) acetylacetonate.

Embodiment 26

The catalyst composition or process of any one of embodiments 1 to 24, wherein the metal-containing salt is selected from the group consisting of yttrium (III) 2-ethylhexonate, yttrium (III) naphthoate, yttium (III) naphthenate, yttrium (III) neodecanoate, yttrium (III) oxalate nonahydrate, yttrium (III) i-propoxide, and combinations thereof.

Embodiment 27

The catalyst composition or process of any one of embodiments 1 to 24, wherein the metal-containing salt is selected from the group consisting of tris(butylcyclopentadienyl)yttrium, tri(n-propylcyclopentadienyl)yttrium, tris(2,2,6,6-tetramethyl-3,5-heptanedionato)yttrium, yttrium (III) 2-ethylhexanoate, yttrium (III) i-propoxide, and combinations thereof.

Embodiment 28

The catalyst composition or process of any one of embodiments 1 to 24, wherein the metal is selected from Group 2 or Group 3.

Embodiment 29

The catalyst composition or process of any one of embodiments 1 to 24, wherein the metal is selected from Group 3.

Embodiment 30

A catalyst composition made according to the process of any one of embodiments 2 to 29.

EXAMPLES

Materials Used

In the examples below, yttrium(III) acetylacetonate ($Y(C_5H_7O_2)_3$), silicon-carbide, yttrium oxide ($Y_2O_3$), and SAPO-34 molecular sieve were used. The SAPO-34 molecular sieve was prepared as described in U.S. Pat. No. 6,812,372, Example 1, column 15, line 33, et seq.

Test Methods

For the purposes of determining the LEI for the following examples in a preferred oxygenate conversion process, methanol is converted to one or more olefin(s) at 475° C., 25 psig (172 kPag) and a methanol weight hourly space velocity of 100 $h^{-1}$. "Lifetime" is defined as the cumulative amount of methanol converted, preferably into one or more olefin(s), per gram of molecular sieve (CMCPS), until the conversion drops to about 10 wt %. If the conversion has not fallen to 10 wt % by the end of the experiment, lifetime is estimated by linear extrapolation based on the rate of decrease in conversion over the last two data points in the experiment.

To obtain reliable and representative data for the products of the reaction process it was necessary to take the weighted average of the selectivity. The weighted averages in Table 1 were calculated based on the following formula: $x_1*y_1+(x_2-x_1)*y_2+(x_3-x_2)*(y_2+y_3)/2+(x_4-x_3)*(y_3+y_4)/2+\ldots$, where "$x_i$" is yield, "$y_i$" is grams of methanol fed per grams of sieve, and "i" is the particular sample number. WHSV was reported based on the weight of the sieve. Methanol converted at less than about 10 wt % conversions was not counted in the calculations. Dimethyl ether (DME) was counted as unreacted methanol in calculating methanol conversion for determining CMCPS. Selectivities were calculated by normalizing the yield data excluding methanol and DME.

The collected effluent samples were analyzed by on-line gas chromatography (Hewlett Packard 6890) equipped with a flame ionization detector. The chromatographic column used was a Q-column.

Catalytic performance of the molecular sieve catalyst composition for conversion of methanol was measured using a micro-reactor unit. All examples used a microflow reactor. Typically, about 115 mg of the catalyst composition was mixed with about 1 g of 100-μm silicon-carbide. The mixture was loaded into the reactor, which is made of about ¼ inch (about 0.635 cm) silicon-steel tubing. The reactor temperature was increased to and then held at about 475° C. while the catalyst was under helium flow (about 46 ml/min) for about 30 to 40 minutes for the temperature to stabilize. Methanol was introduced into the catalyst at about 80 μl/min at a WHSV of about 100 $h^{-1}$, and a pressure of about 25 psig (about 172 kPag) while the effluent was sampled by a 16-loop Valco valve. Typically, about 9 to 15 samples were analyzed to obtain the weighted average selectivity.

Example 1

This catalyst composition was used as the control experiment. It comprised 20 wt % $Y_2O_3$, and was prepared as follows: 800 mg of a SAPO-34 molecular sieve catalyst was weighed and mixed with 200 mg of $Y_2O_3$. The mixture was ground for 30 min with a mortar and pestle to ensure intimate mixing.

Example 2

The catalyst composition using yttrium(III) acetylacetonate was prepared as follows: 0.43 g of $Y(C_5H_7O_2)_3$ was dissolved in 2.0-ml anhydrous methanol. The solution was added dropwise to 1.0 g of a template-containing SAPO-34 molecular sieve. The wetted mixture was mixed with a spatula for a few minutes. The solvent (methanol) was removed by drying the mixture in a vacuum oven at 125° C. for 1 hour. Another 2-ml of methanol solution containing 0.43 g of $Y(C_5H_7O_2)_3$ was added dropwise to the dried mixture followed by mixing with a spatula and further drying at 125° C. in a vacuum oven for 1 hour. The sample was then calcined at 650° C. for 6 hrs in air prior to catalyst testing. The catalyst composition contained roughly 25 wt % of $Y_2O_3$ calculated based on the amount of $Y(C_5H_7O_2)_3$ added, and assuming that substantially all of the yttrium salt was converted to yttrium oxide by the calcination.

Example 3

The catalyst composition using yttrium(III) acetylacetonate was prepared as follows: 0.43 g of $Y(C_5H_7O_2)_3$ was dissolved in 2.0-ml anhydrous methanol. The solution was added dropwise to 1.0 g of a template-containing SAPO-34 molecular sieve. The wetted mixture was mixed with a spatula for a few minutes. The solvent (methanol) was removed by drying the mixture in a vacuum oven at 125° C. for 1 hour. The sample was then calcined at 650° C. for 6 hrs in air prior to catalyst testing. The catalyst composition contained roughly 12.5 wt % of $Y_2O_3$ calculated based on the amount of $Y(C_5H_7O_2)_3$ added, and assuming that substantially all of the yttrium salt was converted to yttrium oxide by the calcination.

Example 4

The catalyst composition using yttrium(III) acetylacetonate was prepared as follows: 0.43 g of $Y(C_5H_7O_2)_3$ was dissolved in 2.0-ml anhydrous methanol. The solution was added dropwise to 1.0 g of a template-free SAPO-34 molecular sieve. The wetted mixture was mixed with a spatula for a few minutes. The solvent (methanol) was removed by drying the mixture in a vacuum oven at 125° C. for 1 hour. 1.2-ml of methanol solution containing 0.26 g of $Y(C_5H_7O_2)_3$ was added to the dried mixture followed by mixing with a spatula and further drying at 125 C in a vacuum oven for 1 hour. The sample was then calcined at 650° C. for 6 hrs in air prior to catalyst testing. The catalyst composition contained roughly 20 wt % of $Y_2O_3$ calculated based on the amount of $Y(C_5H_7O_2)_3$ added, and assuming that substantially all of the yttrium salt was converted to yttrium oxide by the calcination.

TABLE 1

| Catalyst Composition | $C_1$ (wt %) | $C_2^=$ (wt %) | $C_2°$ (wt %) | $C_3^=$ (wt %) | $C_3°$ (wt %) | $C_4$s (wt %) | $C_5$+s (wt %) | Coke (wt %) | $C_{2,3}^=$ (wt %) | lifetime | LEI | % change |
|---|---|---|---|---|---|---|---|---|---|---|---|---|
| SAPO-34   | 1.5 | 37.8 | 0.4 | 40.2 | 0.7 | 13.3 | 4.7 | 1.5 | 78.0 | 18.0 | 1.0 | 0% |
| Example 1 | 1.6 | 34.6 | 0.3 | 43.1 | 0.4 | 14.7 | 4.4 | 0.9 | 77.7 | 45.6 | 2.5 | 153% |
| Example 2 | 1.7 | 35.3 | 0.3 | 42.7 | 0.5 | 14.1 | 4.5 | 1.0 | 78.0 | 37.2 | 2.1 | 106% |
| Example 3 | 1.9 | 33.5 | 0.3 | 42.9 | 0.5 | 13.9 | 6.7 | 0.5 | 76.4 | 49.7 | 2.8 | 175% |
| Example 4 | 2.0 | 34.6 | 0.4 | 43.3 | 0.7 | 13.3 | 5.2 | 0.9 | 77.9 | 36.0 | 2.0 | 100% |

Results

In Table 1, $C_1$, $C_2^=$, $C_2°$, $C_3^=$, $C_3°$, $C_4$s, $C_5$+s and $C_{2,3}^=$ refer to methane, ethylene, ethane, propene, propane, butenes and butanes, hydrocarbons that contain five or more carbons, and ethylene and propene, respectively.

The data clearly showed that yttrium(III) acetylacetonate on SAPO-34 in Examples 2-4 gives much better performance than the catalyst composition of the pure SAPO, and in some cases better than Example 1. Example 2 showed an increase in catalyst lifetime of 106% over that of SAPO-34 alone. Example 3, showed an increase in lifetime of 175% over that of SAPO-34 alone. Example 4, showed an increase in lifetime of 100%. Of course, the increase in lifetime always correlates well with a decrease in coke selectivity, which is a much desired outcome.

All documents described herein are incorporated by reference herein, including any priority documents and/or testing procedures. As is apparent from the foregoing general description and the specific embodiments, while forms of the invention have been illustrated and described, various modifications can be made without departing from the spirit and scope of the invention. Accordingly, it is not intended that the invention be limited thereby.

What is claimed is:

1. A methanol-to-olefins conversion catalyst composition comprising:
   a. a first quantity of molecular sieve particles, each of the molecular sieve particles having
      i. an exterior surface;
      ii. an 8-ring structure; and
      iii. [$AlO_4$], [$PO_4$], and optionally [$SiO_4$]corner-sharing tetrahedral units; and
   b. a metal oxide deposited substantially on the exterior surface of the molecular sieve particles, the metal oxide having been deposited by
      i. contacting the molecular sieve particles with a solution of a metal-containing salt and a solvent, the metal-containing salt comprising a salt soluble in water or common organic solvents and a metal selected from the group consisting of Groups 1-12 and the Lanthanides and combinations thereof, the metal-containing salt solution having an anion size larger than the pore size of the molecular sieve particles;
      ii. drying the molecular sieve particles to remove substantially all of the solvent, thereby depositing the metal-containing salt substantially on the exterior surface of the molecular sieve particles; and
      iii. treating the molecular sieve particles under conditions sufficient to form a metal oxide, whereby at least a portion of the metal-containing salt is converted to metal oxide.

2. The catalyst composition of claim 1, wherein the step of treating the molecular sieve particles comprises calcining the molecular sieve particles at a temperature of at least about 200° C. for at least about 1 second.

3. The catalyst composition of claim 1, wherein the metal oxide is substantially not deposited in the pores of the molecular sieve particles.

4. The catalyst composition of claim 1, wherein the step of contacting the molecular sieve particles with a solution of a metal-containing salt and a solvent comprises mixing the molecular sieve particles and the solution.

5. The catalyst composition of claim 1, wherein the molecular sieve particles have a pore size of 5 angstroms or less.

6. The catalyst composition of claim 1, wherein the molecular sieve particles are silicoaluminophosphate molecular sieve particles.

7. The catalyst composition of claim 1, wherein the molecular sieve particles are of the CHA and/or AEI framework types, or mixtures thereof.

8. The catalyst composition of claim 1, wherein the molecular sieve particles have an average particle size of less than about 1 mm.

9. The catalyst composition of claim 1, wherein the molecular sieve particles have an average particle size of less than about 500 microns.

10. The catalyst composition of claim 1, wherein the molecular sieve particles have an average particle size of less than about 150 microns.

11. The catalyst composition of claim 1, wherein the step of treating the molecular sieve particles comprises calcining at a temperature of from about 200° C. to about 800° C. for at least about 1 second.

12. The catalyst composition of claim 1, wherein the step of treating the molecular sieve particles comprises calcining at a temperature of about 300° C. to about 750° C. for at least about 1 second.

13. The catalyst composition of claim 1, wherein the step of treating the molecular sieve particles comprises calcining at a temperature of from about 400° C. to about 700° C. for at least about 1 second.

14. The catalyst composition of claim 1, wherein the step of treating the molecular sieve particles comprises calcining at a temperature of from about 500° C. to about 675° C. for at least about 1 second.

15. The catalyst composition of claim 1, wherein the molecular sieve particles are SAPO-34.

16. The catalyst composition of claim 1, wherein the molecular sieve particles have a pore size of about 3 to about 4.5 angstroms.

17. The catalyst composition of claim 1, wherein the molecular sieve particles have a pore size of about 3.5 to about 4.2 angstroms.

18. The catalyst composition of claim 1, wherein the molecular sieve particles are crystalline silicoaluminophosphate molecular sieve particles substantially of CHA framework type.

19. The catalyst composition of claim 1, wherein the molecular sieve particles are SAPO molecular sieve particles which consist of mixed or intergrown phases of molecular sieves having the CHA and/or AEI framework types.

20. The catalyst composition of claim 1, wherein the metal-containing salt is Yttrium(III) acetylacetonate.

21. The catalyst composition of claim 1, wherein the metal-containing salt is selected from the group consisting of yttrium (III) 2-ethylhexonate, yttrium (III) naphthoate, yttium (III) naphthenate, yttrium (III) neodecanoate, yttrium (III) oxalate nonahydrate, yttrium (III) i-propoxide, and combinations thereof.

22. The catalyst composition of claim 1, wherein the metal-containing salt is selected from the group consisting of tris (butylcyclopentadienyl) yttrium, tri(n-propylcyclopentadienyl) yttrium, tris (2,2,6,6-tetramethyl-3,5 -heptanedionato) yttrium, yttrium (III) 2-ethylhexanoate, yttrium (III) i-propoxide, and combinations thereof.

23. The catalyst composition of claim 1, wherein the metal is selected from Group 2 or Group 3.

24. The catalyst composition of claim 1, wherein the metal is selected from Group 3.

25. A process for preparing a methanol-to-olefins conversion molecular sieve catalyst composition comprising:
   a. obtaining a first quantity of molecular sieve particles, the molecular sieve particles having an exterior surface, an 8-ring structure, and $[AlO_4]$, $[PO_4]$, and optionally $[SiO_4]$ corner-sharing tetrahedral units;
   b. preparing a solution comprising a metal-containing salt and a solvent, the metal-containing salt comprising a salt soluble in water or common organic solvents and a metal selected from the group consisting of Groups 1-12 and the Lanthanides and combinations thereof, the metal-containing salt solution having an anion size larger than the pore size of the molecular sieve particles;
   c. mixing the first quantity of molecular sieve particles with the solution;
   d. drying the molecular sieve particles to remove the solvent, thereby depositing the metal-containing salt substantially on the exterior of the molecular sieve particles; and
   e. calcining the molecular sieve particles at a temperature of at least about 200° C. for at least 1 second, whereby the metal-containing salt is at least partially converted to metal oxide.

26. The process of claim 25, wherein the metal oxide is substantially not deposited in the pores of the molecular sieve particles.

27. The process of claim 25, wherein the step of contacting the molecular sieve particles with a solution of a metal-containing salt and a solvent comprises mixing the molecular sieve particles and the solution.

28. The process of claim 25, wherein the molecular sieve particles have a pore size of 5 angstroms or less.

29. The process of claim 25, wherein the molecular sieve particles are silicoaluminophosphate molecular sieve particles.

30. The process of claim 25, wherein the molecular sieve particles are of the CHA and/or AEI framework types, or mixtures thereof.

31. The process of claim 25, wherein the step of treating the molecular sieve particles comprises calcining at a temperature of from about 200° C. to about 800° C. for at least about 1 second.

32. The process of claim 25, wherein the step of calcining the molecular sieve particles is at a temperature of from about 400° C. to about 700° C. for at least about 1 second.

33. The process of claim 25, wherein the step of calcining the molecular sieve particles is at a temperature of from about 500° C. to about 675° C. for at least about 1 second.

34. The process of claim 25, wherein the molecular sieve particles are SAPO-34.

35. The process of claim 25, wherein the molecular sieve particles have a pore size of about 3 to about 4.5 angstroms.

36. The process of claim 25, wherein the molecular sieve particles are crystalline silicoaluminophosphate molecular sieve particles substantially of CHA framework type.

37. The process of claim 25, wherein the molecular sieve particles are SAPO molecular sieve particles which consist of mixed or intergrown phases of molecular sieves having the CHA and/or AEI framework types.

38. The process of claim 25, wherein the metal-containing salt is Yttrium(III) acetylacetonate.

39. The process of claim 25, wherein the metal-containing salt is selected from the group consisting of yttrium (III) 2-ethylhexonate, yttrium (III) naphthoate, yttium (III) naphthenate, yttrium (III) neodecanoate, yttrium (III) oxalate nonahydrate, yttrium (III) i-propoxide, and combinations thereof.

40. The process of claim 25, wherein the metal-containing salt is selected from the group consisting of tris(butylcyclopentadienyl) yttrium, tri(n-propylcyclopentadienyl) yttrium, tris (2,2,6,6-tetramethyl-3,5 -heptanedionato)yttrium, yttrium (III) 2-ethylhexanoate, yttrium (III) i-propoxide, and combinations thereof.

41. The process of claim 25, wherein the metal is selected from Group 2 or Group 3.

42. A methanol-to-olefins conversion catalyst composition prepared according to a process comprising the steps of:
   a. obtaining a first quantity of molecular sieve particles, the molecular sieve particles having an exterior surface, an 8-ring structure, and [AlO$_4$], [PO$_4$], and optionally [SiO$_4$]corner-sharing tetrahedral units;
   b. preparing a solution comprising a metal-containing salt and a solvent, the metal-containing salt comprising a salt soluble in water or common organic solvents and a metal selected from the group consisting of Groups 1-12 and the Lanthanides and combinations thereof, the metal-containing salt solution having an anion size larger than the pore size of the molecular sieve particles;
   c. mixing the first quantity of molecular sieve particles with the solution;
   d. drying the molecular sieve particles to remove the solvent, thereby depositing the metal-containing salt substantially on the exterior of the molecular sieve particles; and
   e. calcining the molecular sieve particles at a temperature of at least about 200° C. for at least 1 second.

43. The catalyst composition of claim 42, wherein the step of contacting the molecular sieve particles with a solution of a metal-containing salt and a solvent comprises mixing the molecular sieve particles and the solution.

44. The catalyst composition of claim 42, wherein the molecular sieve particles are silicoaluminophosphate molecular sieve particles.

45. The catalyst composition of claim 42, wherein the molecular sieve particles are of the CHA and/or AEI framework types, or mixtures thereof.

46. The catalyst composition of claim 42, wherein the step of treating the molecular sieve particles comprises calcining at a temperature of from about 200° C. to about 800° C. for at least about 1 second.

47. The catalyst composition of claim 42, wherein the step of calcining the molecular sieve particles is at a temperature of from about 500° C. to about 675° C. for at least about 1 second.

48. The catalyst composition of claim 42, wherein the molecular sieve particles are SAPO-34.

49. The catalyst composition of claim 42, wherein the molecular sieve particles are crystalline silicoaluminophosphate molecular sieve particles substantially of CHA framework type.

50. The catalyst composition of claim 42, wherein the molecular sieve particles are SAPO molecular sieve particles which consist of mixed or intergrown phases of molecular sieves having the CHA and/or AEI framework types.

51. The catalyst composition of claim 42, wherein the metal-containing salt is Yttrium(III) acetylacetonate.

52. The catalyst composition of claim 42, wherein the metal-containing salt is selected from the group consisting of yttrium (III) 2-ethylhexonate, yttrium (III) naphthoate, yttium (III) naphthenate, yttrium (III) neodecanoate, yttrium (III) oxalate nonahydrate, yttrium (III) i-propoxide, and combinations thereof.

53. The catalyst composition of claim 42, wherein the metal-containing salt is selected from the group consisting of tris(butylcyclopentadienyl) yttrium, tri(n- propylcyclopentadienyl) yttrium, tris (2,2,6,6-tetramethyl-3,5 -heptanedionato)yttrium, yttrium (III) 2-ethylhexanoate, yttrium (III) i-propoxide, and combinations thereof.

54. The catalyst composition of claim 42, wherein the metal is selected from Group 2 or Group 3.

* * * * *